(12) United States Patent
Schostek et al.

(10) Patent No.: US 10,820,788 B2
(45) Date of Patent: Nov. 3, 2020

(54) CAPSULE ENDOMICROSCOPE FOR ACQUIRING IMAGES OF THE SURFACE OF A HOLLOW ORGAN

(71) Applicant: Ovesco Endoscopy AG, Tubingen (DE)

(72) Inventors: Sebastian Schostek, Tubingen (DE); Alyssa Albiez, Tubingen (DE); Marc O. Schurr, Tubingen (DE)

(73) Assignee: OVESCO ENDOSCOPY AG, Tubingen (DE)

( * ) Notice: Subject to any disclaimer, the term of this patent is extended or adjusted under 35 U.S.C. 154(b) by 201 days.

(21) Appl. No.: 15/803,573

(22) Filed: Nov. 3, 2017

(65) Prior Publication Data
US 2018/0125343 A1 May 10, 2018

(30) Foreign Application Priority Data
Nov. 4, 2016 (EP) .................................. 16197309

(51) Int. Cl.
*A61B 1/04* (2006.01)
*A61B 1/00* (2006.01)
(Continued)

(52) U.S. Cl.
CPC ............ *A61B 1/041* (2013.01); *A61B 1/0002* (2013.01); *A61B 1/00016* (2013.01);
(Continued)

(58) Field of Classification Search
CPC ..................... H04N 2005/2255; H04N 5/2256
See application file for complete search history.

(56) References Cited

U.S. PATENT DOCUMENTS 5,840,014 A 11/1998 Miyano et al.
2005/0004474 A1\* 1/2005 Iddan ................. A61B 1/00158
600/476
(Continued)

FOREIGN PATENT DOCUMENTS

CN 201790785 U 4/2011
CN 102370453 A 3/2012
(Continued)

OTHER PUBLICATIONS

Machine Translation of WO 2014/041618 Suzuki, Capsule Endoscope, 2014.\*
(Continued)

*Primary Examiner* — Michael J Carey
*Assistant Examiner* — Minqiao Huang
(74) *Attorney, Agent, or Firm* — RatnerPrestia

(57) ABSTRACT

A capsule endomicroscope has a predetermined axial length and a diameter smaller than the axial length. The endomicroscope can acquire images of a surface of a hollow organ, and includes a microscopic image acquisition assembly having an optical axis oriented in a radial direction of the endomicroscope to acquire microscopic images of a section of the surface of a hollow organ present in a predetermined image acquisition area on a radial outer surface of the endomicroscope through a housing of the endomicroscope that has sectionally light-transparent material. A light source emits light rays in a radial direction through the light-transparent material of the housing during image acquisition. The light source and the light-transparent material of the housing located between the light source and the predetermined image acquisition area are interconnected to each other such that no refraction interface exists between the light source and the image acquisition area.

11 Claims, 9 Drawing Sheets

(51) Int. Cl.
  *A61B 1/06* (2006.01)
  *A61B 5/00* (2006.01)
  *G02B 6/42* (2006.01)
  *A61B 90/20* (2016.01)
  *H04N 5/217* (2011.01)
  *H04N 5/225* (2006.01)
  *H04N 5/232* (2006.01)

(52) U.S. Cl.
  CPC ........ *A61B 1/00177* (2013.01); *A61B 1/0615* (2013.01); *A61B 1/0661* (2013.01); *A61B 1/0684* (2013.01); *A61B 90/20* (2016.02); *G02B 6/42* (2013.01); *A61B 5/6861* (2013.01); *A61B 2562/162* (2013.01); *H04N 5/217* (2013.01); *H04N 5/2256* (2013.01); *H04N 5/232* (2013.01); *H04N 2005/2255* (2013.01)

(56) References Cited

U.S. PATENT DOCUMENTS

| | | | |
|---|---|---|---|
| 2006/0079728 A1* | 4/2006 | Kuiper | A61B 1/0019 600/9 |
| 2006/0155174 A1* | 7/2006 | Glukhovsky | A61B 1/00036 600/301 |
| 2006/0170328 A1* | 8/2006 | Kubota | A61B 1/00096 313/495 |
| 2007/0004966 A1 | 1/2007 | Yoshino | |
| 2007/0221233 A1* | 9/2007 | Kawano | A61B 1/00016 128/899 |
| 2009/0124852 A1* | 5/2009 | Suzuki | A61B 18/1445 600/106 |
| 2009/0124853 A1 | 5/2009 | Gono et al. | |
| 2010/0010305 A1* | 1/2010 | Kawano | A61B 1/0005 600/118 |
| 2010/0056869 A1* | 3/2010 | Hayakawa | A61B 1/00096 600/180 |
| 2010/0130822 A1* | 5/2010 | Katayama | A61B 1/00147 600/118 |
| 2011/0319717 A1* | 12/2011 | Pascal | A61B 1/06 600/177 |
| 2013/0172672 A1* | 7/2013 | Iddan | A61B 1/00158 600/109 |
| 2016/0058272 A1* | 3/2016 | Omote | A61B 1/041 600/109 |

FOREIGN PATENT DOCUMENTS

| | | |
|---|---|---|
| IL | 161202 B | 1/2011 |
| WO | 2014/041618 A1 | 3/2014 |

OTHER PUBLICATIONS

Chinese Office Action for Chinese Application No. 201711065598.2, dated Jan. 19, 2020, with translation, 11 pages.
European Patent Office, Extended European Search Report dated May 15, 2017 in European application No. 16197309.4, 8 pages.

* cited by examiner

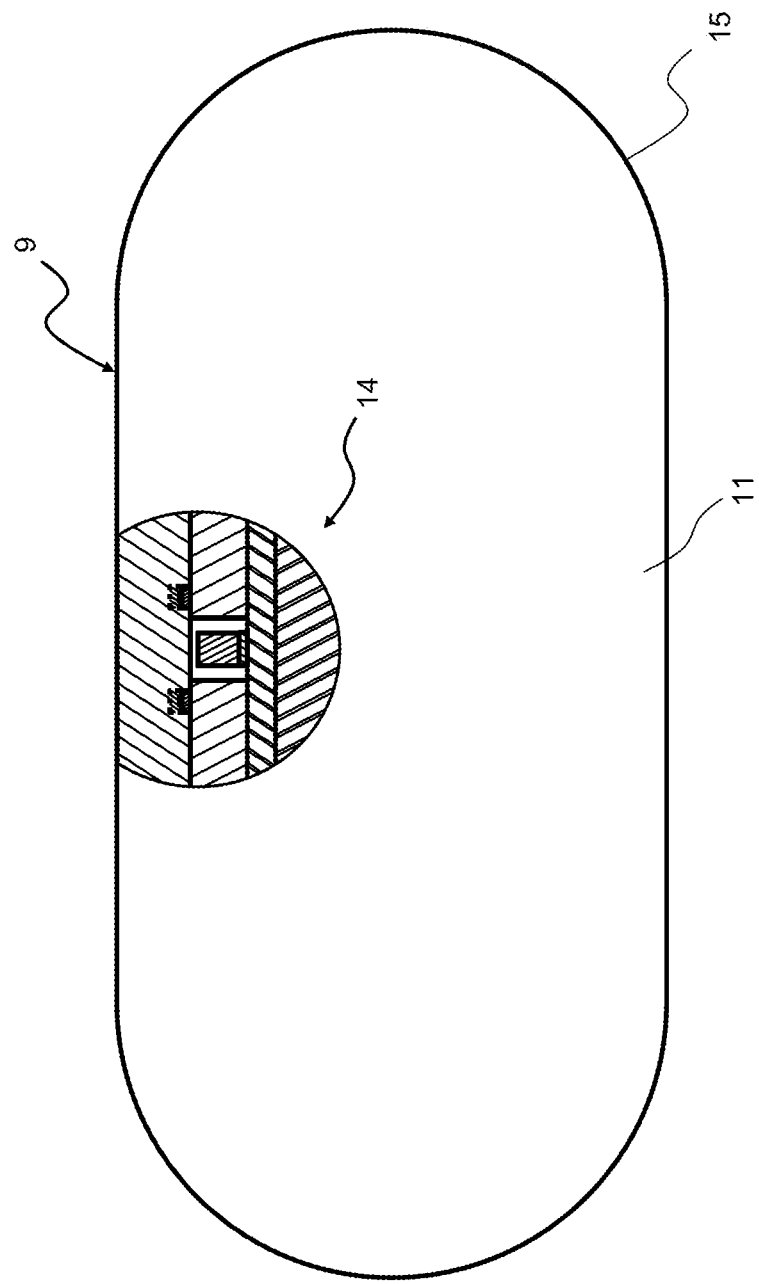

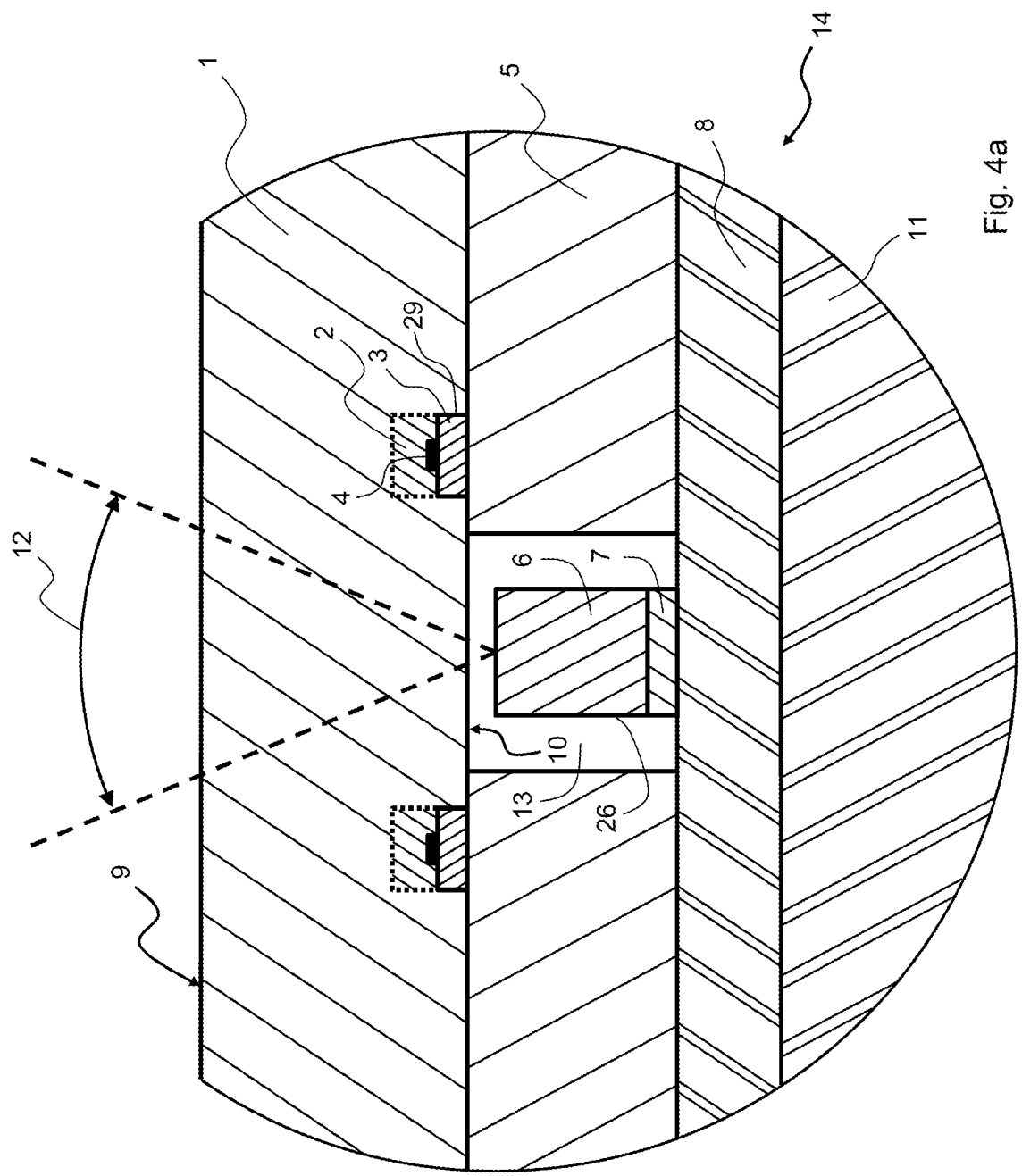

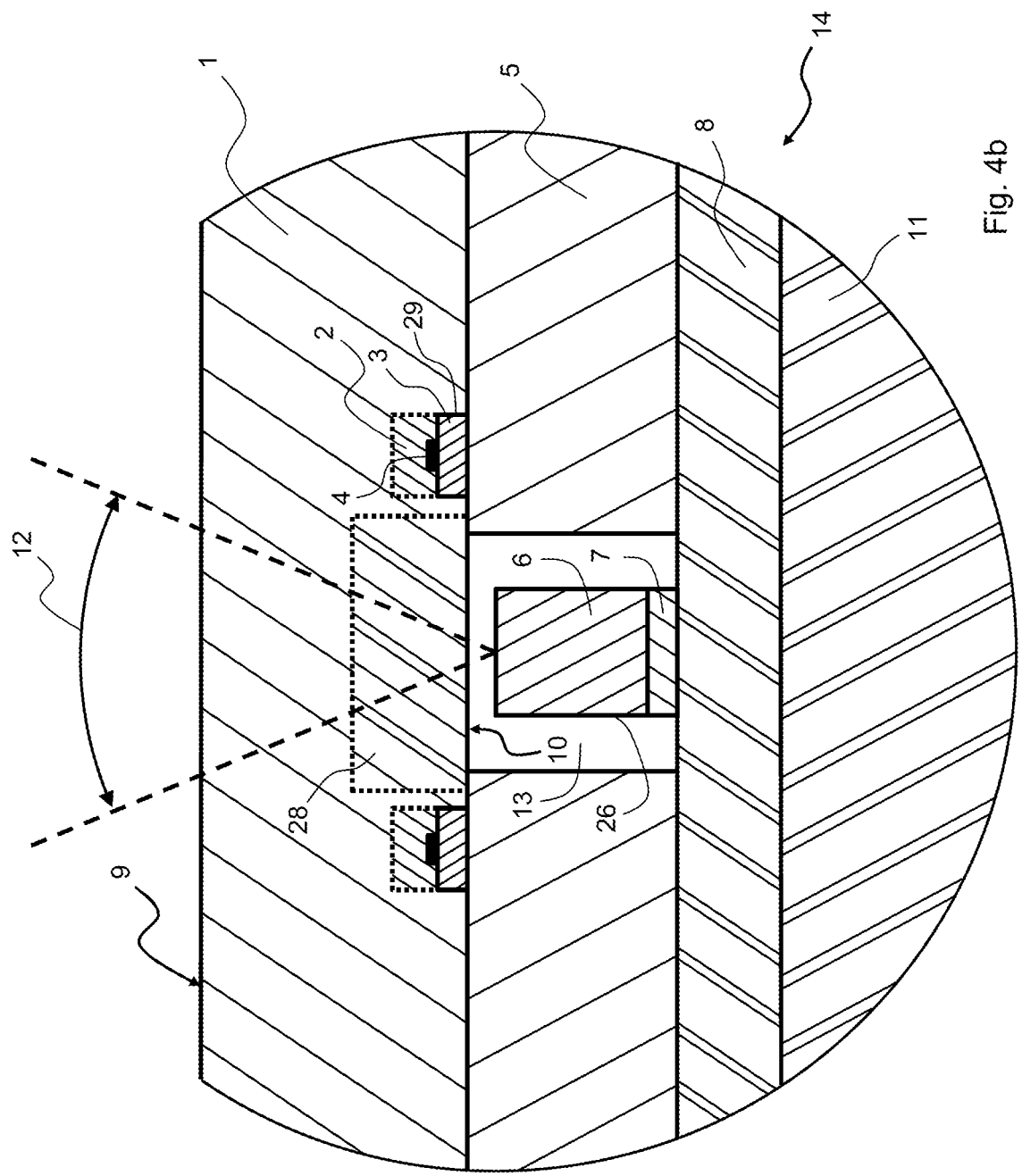

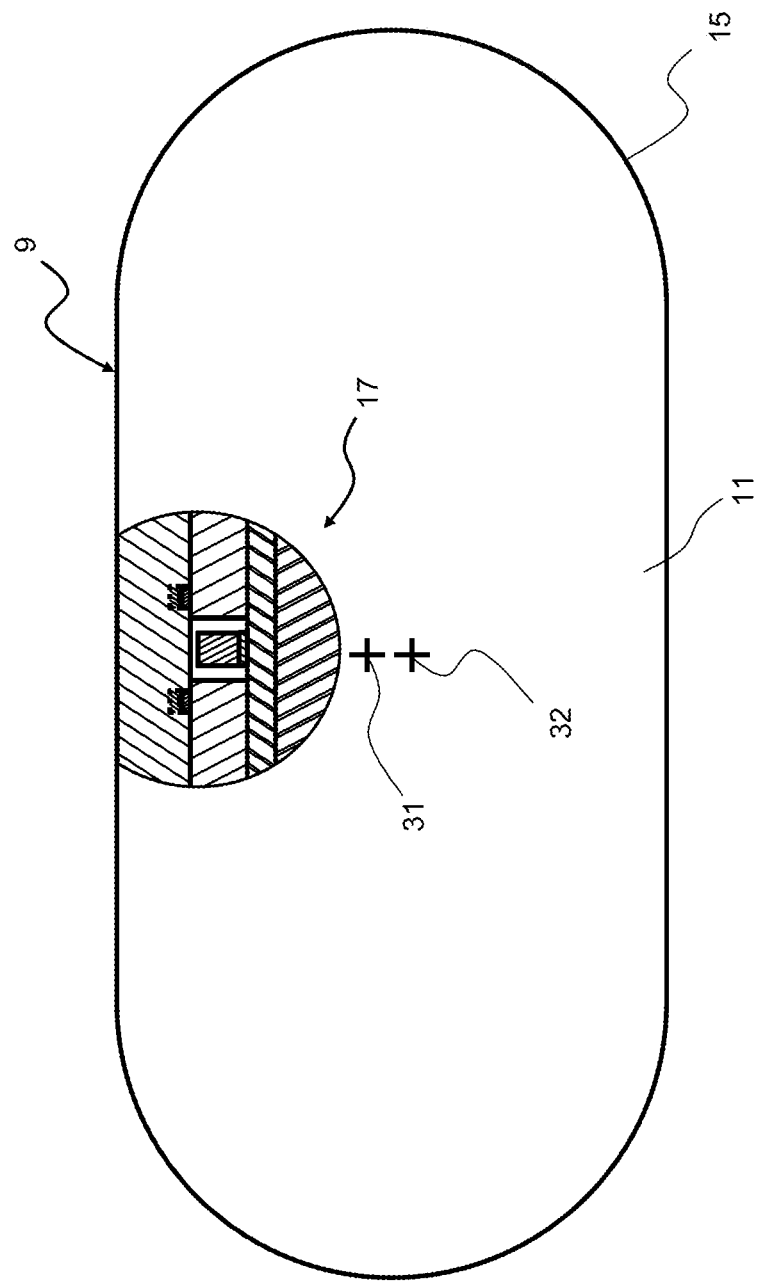

CAPSULE ENDOMICROSCOPE FOR ACQUIRING IMAGES OF THE SURFACE OF A HOLLOW ORGAN

FIELD

The present invention concerns a capsule endomicroscope for acquiring images of the surface of a hollow organ.

BACKGROUND

In recent years, the use of capsule endoscopes has gained wide popularity, as capsule endoscopes offer an easy and painless way of acquiring images of organs such as the small intestine that can otherwise only be acquired through rather cumbersome methods.

Capsule endoscopes can simply be swallowed by a patient and travel through the gastro-intestinal tract capturing data in determined time intervals during their journey. Hence, capsule endoscopes generally comprise some sensor, a data processing unit, an energy source and a data storage unit or a data transmission unit.

In order to achieve good biocompatibility as well as good data capture, the outer housing of such capsule endoscopes has to be carefully designed to ensure the capsule endoscope is resistant to the milieu of the intestinal tract, e.g. acid in the stomach, while still allowing the sensor to function optimally. Hence, in case of an optical sensor, the outer housing is preferentially made of an optically transparent material that does not obstruct the path of light being emitted by light sources or being captured by the sensor.

Conventional capsule endoscopes often comprise an optical sensor e.g. a camera for capturing the lumen of the gastro-intestinal tract. In other words, conventional capsule endoscopes generally capture macroscopic images of the gastro-intestinal tract. This wide-field macroscopic capture of, ideally, the whole surface area of the hollow organ allows to pinpoint smaller local foci of pathology on the surface of the hollow organ, but does not allow for small-scale, high-resolution or even microscopic images of the foci of pathology.

Conventional capsule endoscopes are generally unsuitable for such a close-up capture due to the configuration of their components and due to the fact that capturing the entire surface area of the hollow organ at such a high resolution would lead to an unmanageable amount of data. A capsule endoscope in which the amount of data generated is reduced by controlling data capture in dependency of the movement of the capsule endoscope is known from EP15196319.

SUMMARY

The problem to be solved by the present invention is to provide a capsule endomicroscope that allows for better-quality capture of hollow organs, especially of microscopic structures at the surface of a hollow organ.

This problem is solved by a capsule endomicroscope having a predetermined axial length and a diameter being smaller than the axial length the capsule endomicroscope being adapted to acquire images of a surface of a hollow organ. The capsule endomicroscope comprises a microscopic image acquisition assembly the optical axis thereof is orientated into the radial direction of the capsule endomicroscope in a way to acquire microscopic images of a section of the surface of a hollow organ present in a predetermined image acquisition area on an radial outer surface of the capsule endomicroscope through a housing of the capsule endomicroscope comprising/consisting of at least sectionally light-transparent material, i.e. material that is at least in sections light-transparent. It further comprises a light source adapted to emit light rays in the radial direction of the capsule endomicroscope through the light-transparent material of the housing during image acquisition, wherein the light source and the light-transparent material of the housing located between the light source and the predetermined image acquisition area are interconnected to each other such that no refraction interface exists between the light source and the predetermined image acquisition area.

A refraction interface is defined as non-existing/avoided/prevented, if the refraction interface influences light traveling through the refraction interface for illumination or image acquisition or the like to a not more than insignificant extent. In particular, refraction or reflection occurring at the refraction interface is essentially insignificant for image acquisition according to this invention. A non-existing refraction interface may be the interface between two different materials, the refraction indices of which are essentially equal or comparable such that refraction or reflection occurring at this interface is essentially insignificant for image acquisition according to this invention. For example, at the interface of polycarbonate with a refractive index of 1.59 and epoxy resin with a refractive index of 1.55 to 1.63, no significant refractive effect exists due to the small difference in refractive indices of max. 0.04. Therefore, the refraction interface between polycarbonate and epoxy resin is considered non-existing/avoided/prevented. On the other hand, at the interface between polycarbonate and air with a refractive index of 1.00, the refractive effect is more than insignificant with a large difference of 0.55. Therefore, such a refraction interface between polycarbonate and air exists (e.g. in case of a gap).

The invention aims at improving image quality by reducing the light noise generated by undesired light diffusion from the light source into the image acquisition assembly directly or due to the refractive effects of the material constituting the capsule endomicroscope to a minimum. By constructing the capsule endomicroscope in such a way that no refraction interface exists I is generated between the light source and the predetermined image acquisition area, undesired light scattering and hence, light noise is reduced.

A "microscope" in the sense of the present patent application is any device capable of visualizing/capturing images of structures that cannot be seen by the naked eye. Especially any device capable of visualizing/capturing images of structures of only several micrometers, i.e. less than one millimeter, in size is meant by the term microscope. The light source/illumination means of a capsule endomicroscope according to the present invention may be a LED (light-emitting diode). A microscopic image acquisition assembly/microscopic image acquisition means/contact imaging unit in the sense of the present patent application is an assembly/means/unit that is adapted to capture microscopic images. The microscopic image acquisition assembly/microscopic image acquisition means/contact imaging unit generally comprises an optical module of several lenses and an optical sensor preferentially in the form of a light-sensitive CMOS (Complementary metal-oxide-semiconductor)-chip. The image acquisition area is that area of the surface of the capsule endomicroscope where light rays travelling from are captured by the image acquisition assembly. The microscopic image acquisition assembly acquires microscopic images through the housing of the capsule endomicroscope. The shape, size and positioning of the image acquisition area on the surface area of the capsule endomicroscope can hence be predetermined through the geometric arrangement of the light source, image acquisition assembly and outer housing of the capsule endomicroscope.

The light source and the light-transparent material of the housing located between the light source and the predetermined image acquisition area can be interconnected to each other/connected with each other by casting technique/grouting technique. The light source can be connected to the light-transparent material of the housing by directly pressing/press-fitting/embedding the light source into the light-transparent material of the housing or by casting the light-transparent material of the housing onto the light source. Importantly, no gaps are present between the light source and the light-transparent material, so no refractive interface is generated at the boundary between the light source and the light-transparent material. Thus, the light source can be directly incorporated into the light-transparent material of the housing.

Alternatively, the light source can be directly incorporated/embedded into a separate component of a light-transparent material and said separate component is directly incorporated into the light-transparent material of the housing. The light source may be incorporated into the separate component by casting/grouting/press-fitting/embedding or a similar technique and the separate component may be incorporated into the light-transparent material of the housing by casting/grouting/press-fitting/embedding or a similar technique.

According to an advantageous aspect of the invention, the light-transparent material of the separate component into which the light source is incorporated and the light-transparent material of the housing into which the separate component is incorporated have essentially the same refractive index.

In order to further improve image quality, according to another advantageous aspect of the invention, the microscopic image acquisition assembly is arranged in a dedicated lumen that is equipped with a separate distortion prevention component. This separate distortion prevention component is separate from the optically transparent material of the housing of the capsule endomicroscope located between that side of the lumen closest to the predetermined image acquisition area. The distortion prevention component is adapted to form the boundary of the lumen on that side of the lumen closest to the predetermined image acquisition area and is further adapted to prevent any refraction interface from arising/being generated at the boundary between a fluid present in the lumen and the distortion prevention component. The distortion prevention component is separate in a sense that it is essentially part of an assembly and does not exclude that the distortion prevention component is an integral part of an assembly achieved by press-fitting, grouting, embedding, potting. In other words, the distortion prevention component is separate in the sense that it is a distinct and discrete entity/component, that, however, may be incorporated/integrated into a larger assembly of components, e.g. by press-fitting, grouting, embedding, potting.

The dedicated lumen contains is a hollow space that may contain air or another gas. Therefore, a refraction interface is formed between the lumen and the distortion prevention component. The surface of the distortion prevention component that forms said refraction interface is critical for ensuring the effect of this interface to remain insignificant for image acquisition.

For this purpose, the distortion prevention component has, at least on that part of the distortion prevention component forming the boundary of the lumen, a predetermined surface structure adapted to reduce refraction at the surface of the distortion prevention component. For example, the distortion prevention component can be a plate of light-transparent material with a very smooth surface. Such a smooth surface may be achieved by polishing. Such a plate of polished light-transparent material can easily be manufactured and a very high degree of reproducibility can be achieved in determining the quality/characteristics of the surface of such a plate. The distortion prevention component can generally be a plate-like or brick-like component that is interconnected with the light-transparent material by press-fitting, grouting, embedding, potting. The distortion prevention component can thus be an inlay in the light-transparent material. Alternatively, the distortion prevention component can also be deposited onto the inner surface of the light-transparent material.

In order to further reduce light noise and to increase the effectiveness of illumination, the light source may be located as distal as possible from the center of the capsule endomicroscope in radial direction in the housing of the capsule endomicroscope. The light source may be integrated into that material of the capsule endomicroscope that also constitutes the outer boundary or surface layer of the capsule endomicroscope.

The light source can be realized as one or more LEDs and the image acquisition assembly can be a camera comprising a lens assembly and CMOS-chip. By integrating the light source into a most peripheral layer of the housing of the capsule, the light source is arranged as close to the object to be captured as possible. This arrangement increases the efficacy of illumination, as light emitted from the light source has to travel only a short distance to the object to be captured, thus losses due to undesired light scattering or refraction are minimized. In addition to that, this arrangement minimizes the chance of light emitted from the light source directly being captured in the image acquisition assembly, which leads to blurring, reflections and a general degradation of image quality.

If the light source is located as close as possible to the object to be captured and preferentially closer to the object to be captured than the image acquisition assembly, light emitted by the light source can essentially only reach the image acquisition assembly after having impinged on the object to be captured and after having been reflected back. Also, the image acquisition assembly can be arranged in radial direction closer to the central longitudinal axis of the capsule endomicroscope or arranged more towards the interior of the capsule endomicroscope than the light source.

Thus, the arrangement of the light source and of the image acquisition assembly is carefully configured in order to minimize the interference of light emitted from the light source with the image acquisition carried out by the image acquisition assembly.

Apart from the configuration or arrangement of the functional components of the capsule endomicroscope, the choice of materials selected for the manufacturing of the components of the capsule endomicroscope relevant to the image acquisition process is also determined by the goal of improving image quality. According to this aspect, especially choosing materials with an essentially equal refractive index along the light path for image acquisition and/or illumination serves to improve image quality.

Thus, the material present between the predetermined image acquisition area on the outer surface of the capsule endomicroscope and the image acquisition assembly and/or the light source preferentially has an essentially constant refractive index.

This means, that light emitted from the light source towards the object to be captured encounters material of essentially the same refractive index along its entire path from the light source at least to the most peripheral layer of the multi-layer housing of the capsule endomicroscope. Similarly, light being reflected from the object to be captured encounters material of essentially the same refractive index along its entire path from the object to be captured or at least from the most peripheral layer of the multi-layer housing of the capsule endomicroscope to the image acquisition assembly.

This selection of materials with essentially the same refractive index along the entire path of the light rays/beams allows a reduction in undesired light scattering or light deflection/refraction due to refractive interfaces arising at the boundary of two adjacent materials of differing refractive indices. Thus, by carefully choosing the materials along the light path in order to avoid differences in refractive indices, image quality can be further improved.

According to yet a further aspect of the invention, the material present between the predetermined image acquisition area on the outer surface of the capsule endomicroscope and the lumen containing the image acquisition assembly and/or the light source entirely consists of one solid material or multiple solid materials, By only using solid materials in the light path, but no liquids or gases, undesired effects due to large differences in refractive indices can be further reduced.

In order to prevent a refraction interface arising at the boundary between the lumen filled with a fluid e.g. air and/or solid and the surrounding material, according to an aspect of the invention the lumen can be equipped with a distortion prevention component arranged between the image acquisition assembly and the predetermined image acquisition area on the outer surface of the capsule endomicroscope. This distortion prevention component preferentially is a component of a light-transparent material having a defined and predetermined surface structure.

According to a further aspect of the invention, the center of gravity of the capsule endomicroscope is displaced from the geometric center point of the capsule endomicroscope. This brings the microscopic image acquisition assembly and the light source closer to the object to be captured, as the position of the capsule endomicroscope is tilted in such a way that that part of the outer surface of the capsule endomicroscope containing the image acquisition area is preferentially pressed against the object to be captured, e.g. the tissue of a hollow organ. Thus, a direct contact is established between the tissue to be imaged and the microscopic image acquisition assembly which hence can also be referred to as a contact imaging unit/contact imaging assembly.

Preferentially, the position of the center of gravity of the capsule endomicroscope is chosen in such a way to cause the capsule endomicroscope to tilt in space from its longitudinal axis in the direction towards the image acquisition area on the outer surface of the capsule endomicroscope. As the capsule endomicroscope travels through the intestinal tract, the inclined position of the capsule endomicroscope causes that side of the capsule endomicroscope containing the image acquisition area to be pressed against the tissue surface. To achieve this effect, the center of gravity of the capsule endomicroscope is preferentially displaced from the geometric center point of the capsule endomicroscope towards the position of the image acquisition area on the outer surface of the capsule endomicroscope.

According to a further aspect of the invention, the capsule endomicroscope comprises a recess in the housing of the capsule endomicroscope. The position of the recess at least in part coincides with the image acquisition area. Preferentially, the image acquisition area is fully contained within the recess.

The recess allows the capture of deformable structural features of the object to be captured in their native configuration. Without a recess, such deformable structures are flattened during the image acquisition process, as the capsule endomicroscope is pressed against the object to be captured.

For example, in the small intestine, intestinal villi project from the intestinal wall into the intestinal lumen. If such intestinal villi are captured with a capsule endomicroscope without a recess at the surface of the capsule endomicroscope, the intestinal villi are flattened against the wall of the small intestine by the capsule endomicroscope. Thus, pathologies in the three-dimensional shape/configuration of the intestinal villi cannot be diagnosed accurately.

The recess allows deformable structures such as intestinal villi to enter the space created by the recess and to adopt their native physiological three-dimensional configuration. As the position of the recess preferentially coincides with the position of the image acquisition area, the intestinal villi contained in the recess can then be captured.

According to a further aspect of the invention, the capsule endomicroscope can further comprise a proximity detection assembly configured to detect the presence of an object in the close proximity of the image acquisition area and, if said detection result is positive, selectively activate/switch on the image acquisition assembly.

This proximity detection assembly serves to improve the efficiency of energy use of the capsule endomicroscope by ensuring that an image acquisition is only carried out, if there is actually an object to be captured in the close or immediate proximity of the capsule endomicroscope, especially of the image acquisition area on the outer surface of the capsule endomicroscope. The proximity detection assembly can for example be an infrared sensor or a small camera.

According to a further aspect of the invention, the capsule endomicroscope can further comprise a macroscopic context image acquisition assembly configured to carry out wide-field macroscopic capturing of the larger surroundings of the capsule endomicroscope, preferentially simultaneously with an image acquisition operation of the image acquisition assembly.

The provision of such a macroscopic context image acquisition assembly is especially useful if the image acquisition assembly of the capsule endomicroscope is configured as a contact image acquisition assembly adapted to provide high resolution close-up images of relatively small areas of an object present in the immediate vicinity of the image acquisition area/directly contacting the image acquisition area on the outer surface of the capsule endomicroscope.

While such a microscopic image acquisition assembly provides a very detailed view of a very small area of the object to be captured, an accurate interpretation of these image data often requires information on the context in which this very detailed view was captured.

For example, the microscopic image acquisition assembly may capture a very detailed microscopic image of a small area containing intestinal villi. In order to accurately diagnose whether the morphology of the intestinal villi captured is normal, however, it is necessary to have information on the position within the intestinal tract in which this small area was captured. Hence, information is required whether this image was captured by the image acquisition assembly e.g. in the esophagus or e.g. in the small intestine.

Thus, the macroscopic context image acquisition assembly captures the bigger picture of the surroundings of the capsule endomicroscope, i.e. the lumen of the gastrointestinal tract, thereby providing the context of the information acquired by the image acquisition assembly. Preferentially, the context image acquisition assembly captures/images the larger surroundings of the capsule endomicroscope at the same time as the image acquisition assembly captures/images the object present in the image acquisition area on the outer surface of the capsule endomicroscope.

The different functions of the context image acquisition assembly and the image acquisition assembly are preferentially also reflected in their positioning on the capsule endomicroscope with the image acquisition assembly advantageously arranged at a side/radially peripheral surface of the capsule endomicroscope so to be pressed against a wall of a hollow organ as the capsule travels through the gastrointestinal tract and the context image acquisition assembly preferentially being arranged at the front or rear end of the capsule endomicroscope so to image a section of the lumen of the hollow organ.

The capsule endomicroscope may also further contain a telemetry-unit for sending data to an extra-corporeal receiver unit or for receiving data from an extra-corporeal transmitter unit.

Another aspect of the invention concerns a method of acquiring microscopic images of a surface of a hollow organ using a capsule endomicroscope according to the present invention. According to this method, the space/spaces between the surface of the capsule endomicroscope and the surface of the hollow organ is filled with a fluid and/or substance selected to avoid/dissolve any refractive interfaces between the surface of the capsule endomicroscope and the fluid. Through the use of such a fluid, no refraction interface arises between the image acquisition area on the surface of the capsule endomicroscope and the surrounding fluid and/or substance, or the effect of a refraction interface is significantly diminished Such a fluid can be, for example, polyethylene glycol with a refraction index of 1.47 which is close to the refraction index of a typical housing material. The fluid and/or substance can be selected to have the same or essentially the same refractive index as the light-transparent material of the housing of the capsule endoscope.

In cases in which a capsule endomicroscope with a recess at the surface of the capsule endoscope is used for image acquisition, it is important that the recess is filled with the fluid selected to avoid any refractive interfaces between the surface of the capsule endomicroscope in the recess and the fluid and/or substance. As in the recess three-dimensional anatomic structures, e.g. intestinal villi, can adopt their native configuration, ensuring the presence of the fluid/substance in the recess is essential for ensuring a high image quality during the diagnosis of diseases affecting the three-dimensional configuration of such anatomic structures.

BRIEF DESCRIPTION OF THE DRAWING FIGURES

Further features and advantages of the present invention become apparent from the following description of presently preferred embodiments.

In the figures,

FIG. 3 shows a capsule endomicroscope according to the present invention, especially disclosing the constructive features of the microscopic image acquisition assembly/contact imaging unit.

FIGS. 4a and 4b are detailed views of the features of the microscopic image acquisition assembly/contact imaging unit in an embodiment of a capsule endomicroscope adapted for contact imaging of tissue with an essentially smooth tissue surface. FIG. 4a shows a contact imaging unit without a separate component. FIG. 4b shows a contact imaging unit with a separate component.

Figure 5:
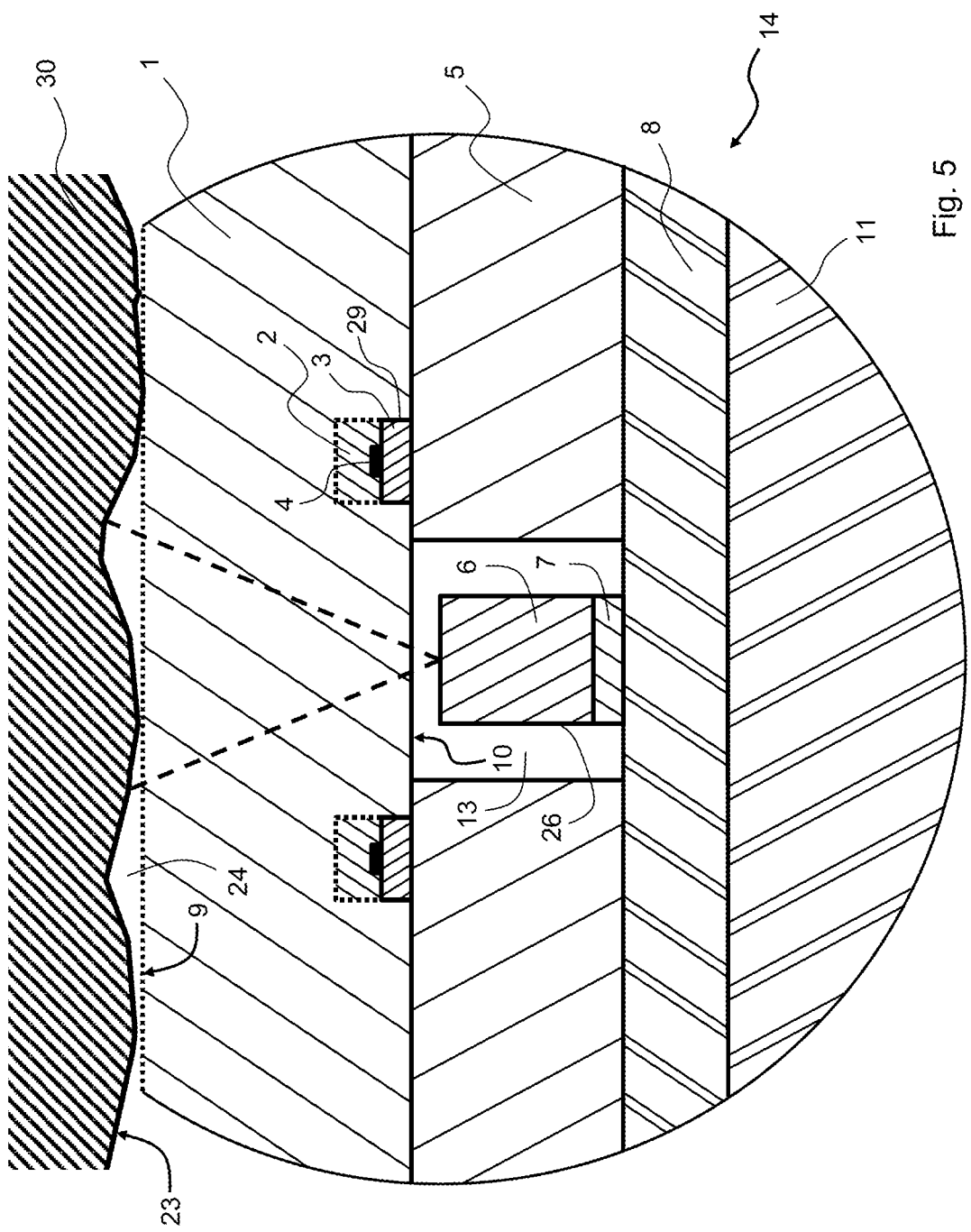

FIG. 5 shows a detailed view of the features of the microscopic image acquisition assembly/contact imaging unit, in an embodiment of a capsule endomicroscope especially adapted for contact imaging of tissue with an essentially smooth tissue surface.

Figure 6:
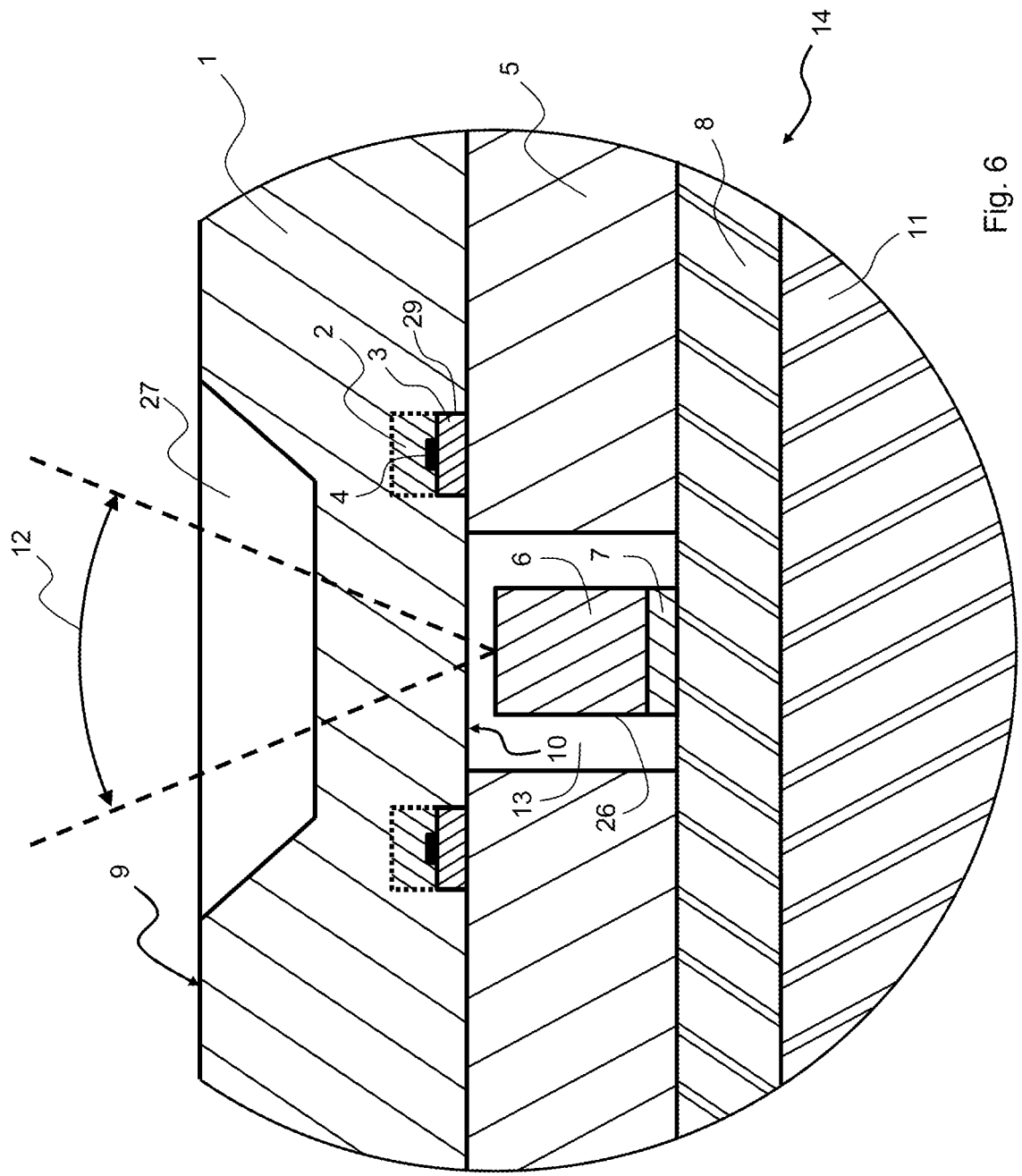

FIG. 6 shows a detailed view of the features of the microscopic image acquisition assembly/contact imaging unit in an embodiment of a capsule endomicroscope especially adapted for contact imaging of tissue with a three-dimensionally structured tissue surface.

Figure 7:
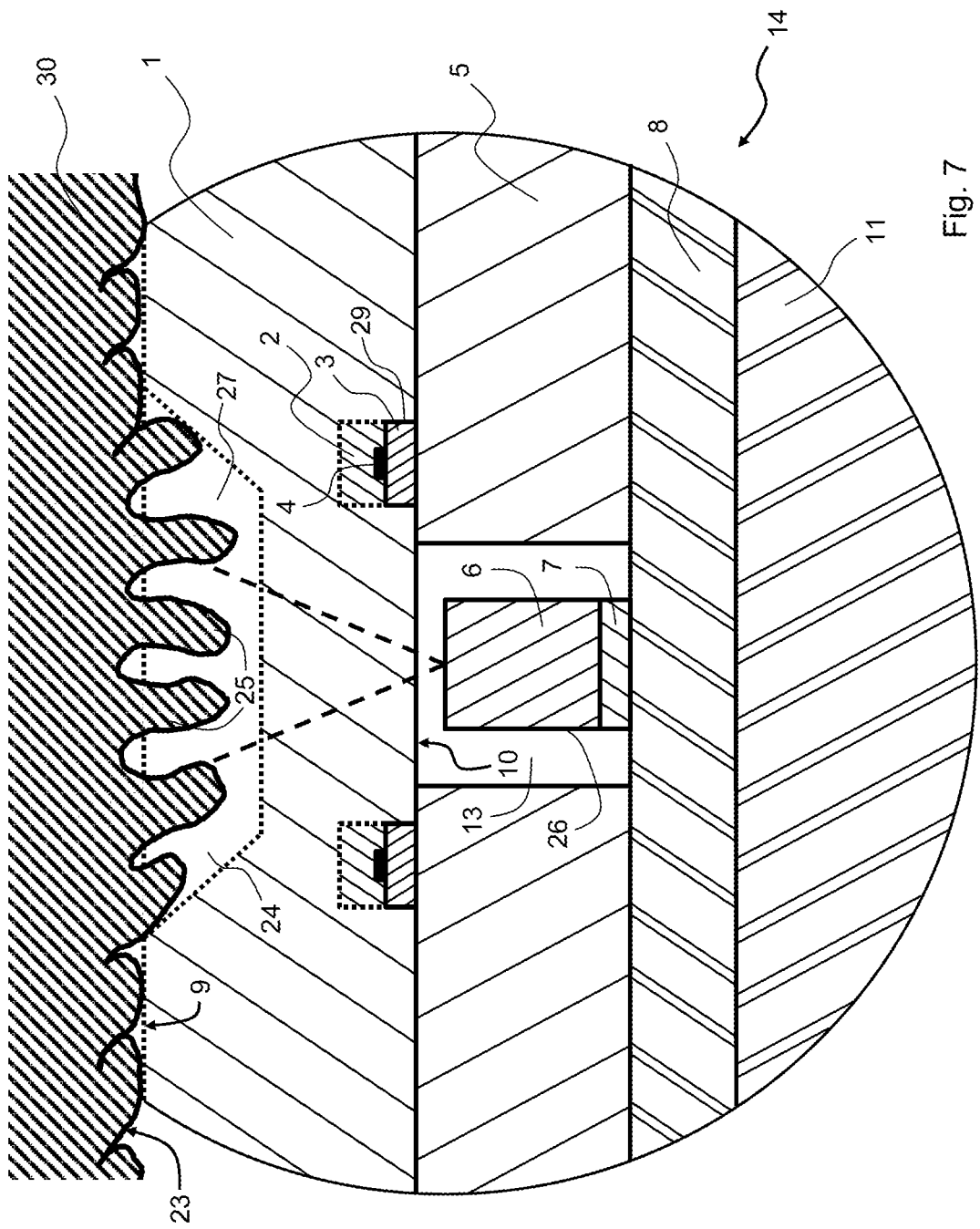

FIG. 7 shows a detailed view of the construction features of the microscopic image acquisition assembly/contact imaging unit and the capturing of a three-dimensionally structured tissue surface.

FIG. 8 shows a capsule endomicroscope according to the present invention, in which the center of gravity and the geometric center point of the capsule endomicroscope are indicated.

DETAILED DESCRIPTION

Figure 1:
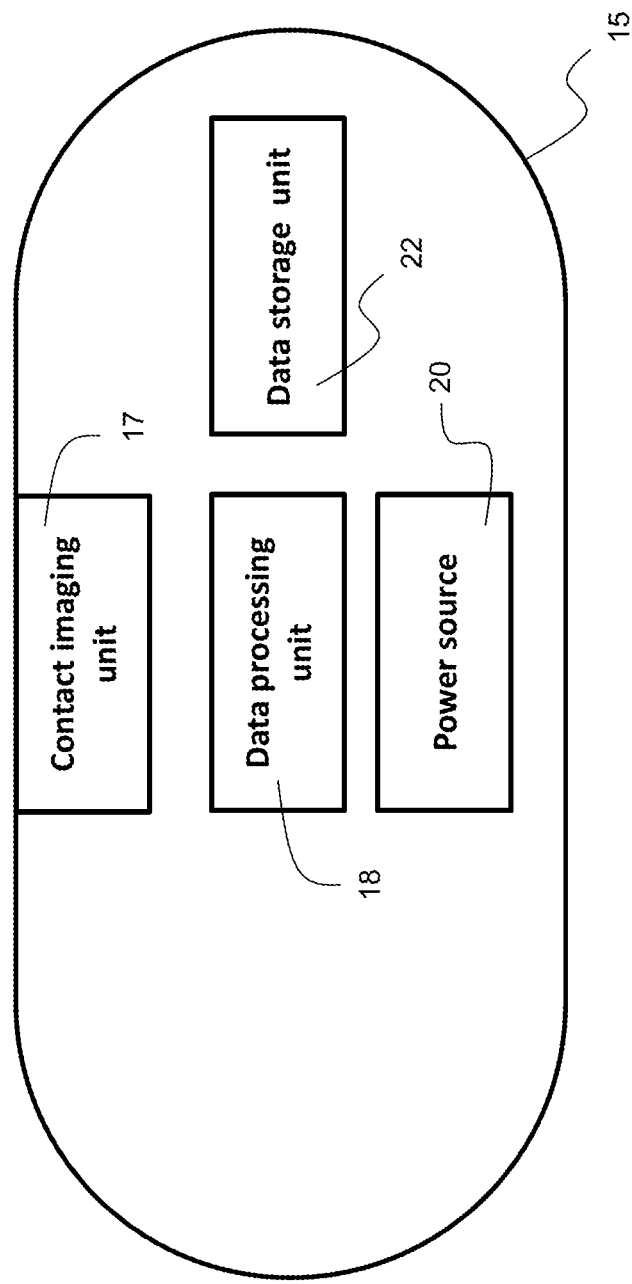
FIG. 1 shows an embodiment of a capsule endomicroscope according to the present invention in which the microscopic image acquisition assembly is a contact imaging unit, and with a data processing unit, a data storage unit and an energy source.

As shown in FIG. 1, a capsule endomicroscope 15 according to the present invention comprises a contact imaging unit 17 as an image acquisition assembly, a data processing unit 18, a data storage unit 22 and a power source 20.

Figure 2:
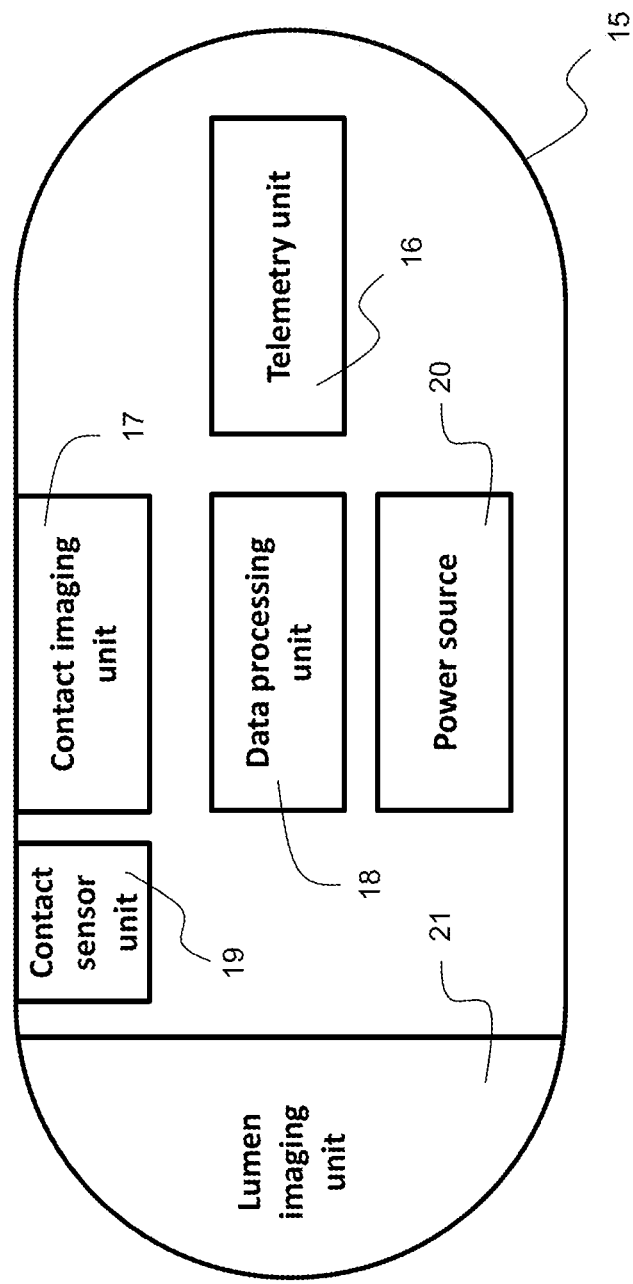
FIG. 2 shows an embodiment of a capsule endomicroscope according to the present invention with a contact imaging unit and a proximity detection assembly/contact sensor, and with a macroscopic context image acquisition assembly/lumen imaging unit and with a data processing unit, a telemetry unit and an energy source.

FIG. 2 shows another capsule endomicroscope 15 according to the present invention comprising the contact imaging unit 17, the data processing unit 18 as well as a telemetry unit 16, a contact sensor unit 19 as a proximity detection assembly and a lumen imaging unit 21 as a context image acquisition assembly.

Other embodiments of the invention can have different combination of features such as the embodiment shown in FIG. 1 with a telemetry unit instead of a data storage unit, or the embodiment shown in FIG. 2 without a proximity detection assembly/contact sensor, or the embodiment shown in FIG. 1 with a proximity detection assembly/contact sensor. Other such combinations are also possible.

As shown in FIG. 3, an outer housing separates the interior 11 of the capsule endomicroscope 15 from the surroundings of the capsule endomicroscope. On the outer housing is the outer capsule surface 9.

Further constructive details of the contact imaging unit 17 become apparent from FIG. 4, in which a detailed view (as indicated by the numeral 14) of the contact imaging unit 17 is shown.

According to this embodiment, the light source/illumination means of the contact imaging unit 17 preferentially contains one or more conventional LEDs 29 that are connected with an optically transparent material 1 forming the outer layer of the outer housing of the capsule endomicroscope 15 in such a way, that the optical refractive interface between the optically transparent material 1 of the housing of the capsule 15 and the optically transparent material 2 of the conventional LED 29 essentially disappears or is dissolved.

This is achieved through the connection of two materials with a similar refractive index preferentially through a form fitting mechanism and/or casting technique. To indicate this dissolution of the refractive interface between said materials/components, in FIGS. 4a, 4b, 5, 6 and 7, the line between the optically transparent material 1 of the housing of the capsule endomicroscope 15 and the optically transparent material 2 of the conventional LED 29 is shown as a dashed line.

Each LED 29 comprises a LED-chip 4 that is mounted onto a substrate material 3 and that is surrounded by and connected with an optically transparent material 2. The optically transparent material 2 of the LED 29 and the optically transparent material 1 of the housing of the capsule endomicroscope 15 are selected in such a way that light emitted from the LED-chip 4 travels exclusively through solid material components preferentially connected to each other by a form-locking mechanism from the LED-chip 4 to the image acquisition area 12 on the capsule surface 9 of the outer housing of the capsule endomicroscope 15.

The outer housing can be formed of only a single layer of material or of multiple layers and separates the interior 11 of the capsule endomicroscope 15 from the surroundings.

In the embodiment according to FIG. 4, the two LED-chips 4 are embedded into the most peripheral layer 1 of the outer housing of the capsule endomicroscope 15 that separates the outer surface 9 of the capsule endomicroscope 15 from the interior 11 of the capsule endomicroscope 15.

The optically transparent material 1 is a solid material and forms a part of the capsule endomicroscope surface 9, especially in the image acquisition area 12. The optically transparent material 1 may be a material composite, wherein optical characteristics, especially refractive indices, within the material composite are essentially equal or constant along the entire path of light travelling from the image acquisition area 12 to the image acquisition assembly 17 and/or to an optical sensor contained within the image acquisition assembly. This helps to prevent distortions or scattering of light at the interface between different materials of differing refractive indices which may reduce the quality of the optical imaging.

In order to achieve high biocompatibility, chemical resistance and/or surface properties of the capsule endomicroscope, a special housing/coating may be deposited on the outer housing of the capsule endomicroscope. This housing/coating may be Parylene.

In such a case the very thin layer of the optical transparent material Parylene may be of a dimension of 10 to 20 micrometers, which does not cause a reduction in the quality of illumination and/or image acquisition even in case of a difference in refractive index between the housing material and the optically transparent material 1. As the layer of Parylene is very thin, a negative impact upon the optical characteristics of the material of the capsule endomicroscope is minimized.

The LEDs 29 are mounted onto a layer of substrate material 5, in which like in an electronic conductor plate the electrical circuits for the operation of the LEDs 29 are integrated. The mounting of the LEDs 29 onto the substrate material 5 can occur through gluing or bonding (direct mounting of the LEDs) or through welding/soldering (mounting of the LEDs as conventional LEDs comprising welding terminals). The LEDs 29 form the light source/illumination means in this embodiment.

In the following, the image acquisition assembly/optical sensor of the contact imaging unit 17 is described.

In this embodiment, the image acquisition assembly is a camera 26. The camera 26 comprises an optical module 6 and an image sensor 7. The geometric configuration and arrangement of the optical module 6 and the image sensor 7 generates an image acquisition area 12 of a predetermined size on the surface 12 of the capsule endomicroscope 15.

The camera 26 is arranged within the capsule endomicroscope 15, so that the image acquisition area 12 is created on the capsule surface 9 in an image acquisition area of a desired size, for example 1×1 millimeter.

In this image acquisition area 12 a tissue surface 23 adjacent to the capsule endomicroscope surface 9 can be detected and captured. It increases imaging quality if the tissue surface 13 is immediately adjacent and actually physically contacts the image acquisition area 12.

In order to increase the efficiency of the light source/illumination means it is advantageous to position the light source/illumination means as close as possible to the imagining area 12 of the capsule surface 9.

In order to simultaneously determine the desired size of the image acquisition area 12 and in order to avoid light emitted from the light source directly being captured by the camera 26, the camera 26 is distanced from the capsule endomicroscope surface 9 further away than the light source/illumination means, i.e. the LEDs 29. For this purpose, the camera 26 can be positioned in a recess or lumen 13 within the substrate material 5, which encases the lumen 13 accommodating the camera 26.

The camera 26 is mounted onto a substrate material 8 arranged closer to a central longitudinal axis of the capsule endomicroscope 15 in radial direction than the substrate layer 5 in which the lumen 13 is formed. In other words, the layer of substrate material 8 is located closer to the interior of the capsule 15 and hence less peripheral than the layers of substrate material 5 and optically transparent material 1.

The lumen 13 around the camera 26 can be filled with a fluid or solid. This solid material can also be part of the optically transparent material 1.

Preferentially, the lumen 13 surrounding the camera 26 is filled with air. The light travelling between the camera 26 and the image acquisition area 12 in this case passes an optical refractive interface on its path from the image acquisition area 12 at the surface 9 of the capsule endomicroscope 15 and the lumen 13 containing the air.

This optical refraction interface is generated through a high difference in refractive indices of, for example, 1.0 for air and 1.5 for the optically transparent material 1. Also, the requirements for the quality of the surface of the boundary surface 10 at the boundary between the air in the lumen 13 and the optically transparent material 1 are high, because irregularities of the surface forming the boundary surface 10 can lead to distortions and reductions in quality of the imaging.

In order to ensure a high quality of the surface forming the boundary surface 10 during the manufacture of the capsule endomicroscope 15 and to prevent the arising of a refraction interface, a distortion prevention component 28, e.g. a component of optically transparent material, can be arranged between the lumen 13 surrounding the camera 26 and the optically transparent material 1.

The distortion prevention component 28 can be a component of a polymer material of a defined and known surface quality and structure as well as of a certain desired refractive index. A capsule endomicroscope 15 with a contact imaging unit 17 comprising a distortion prevention component 28 is shown in FIG. 4b.

The distortion prevention component 28 can form the boundary of the lumen 13 on that side of the lumen 13 that is closest to the image acquisition area 12. The surface of the distortion prevention component can be adjusted to have certain defined characteristics, e.g. to be very smooth and/or regular so that blurring and distortions arising at the interface between the distortion prevention component 28 and the lumen 13 are minimized.

Such a distortion prevention component 28 serves to ensure a sufficient quality of the surface forming the boundary surface 10 without the need for using a casting technique which causes increased complexity, increased costs and limited reproducibility.

In this embodiment, the distortion prevention component 28 is a component of optically transparent material and forms part of the optically transparent material 1. This causes the boundary surface between the distortion prevention component 28 and the rest of the optically transparent material 1 to dissolve. This effect is indicated in FIG. 4b by a dashed line between the distortion prevention component 28 and the optically transparent material 1.

For some applications of the capsule endomicroscope, it is advantageous if the contour of the endomicroscope surface 9 in the image acquisition area 12 essentially follows the contour of the endomicroscope surface along the rest of the capsule endomicroscope 15. In other words, in such an embodiment, the surface of the capsule endomicroscope is essentially smooth and capsule-like without any projections or recesses. Such a capsule endomicroscope 15 is especially suitable for capturing tissue with a smooth surface.

As shown in FIG. 5, a smooth tissue surface 23 of tissue 30 located in direct proximity to the capsule endomicroscope surface 9 in the image acquisition area 12 can be illuminated by the light source and captured by the camera 26.

As both the surface 9 of the capsule endomicroscope 15 and the tissue surface 23 are essentially flat and smooth, direct contact can be established between the tissue surface 23 and the image acquisition area 12. This configuration is especially advantageous for capturing tissue surface in the esophagus.

If a tissue with a three-dimensionally structured surface is to be captured, the capsule endomicroscope 15 can additionally be equipped with a recess 27 as shown in FIGS. 6 and 7.

The image acquisition area 12 preferentially extends within the boundaries of this recess 27. The recess 27 serves to contain structures 25 present at the tissue surface and is configured in such a way that these structures 25 can enter into the space generated by the recess 27 and thereby re-adopt their physiological three-dimensional configuration in a state in which the capsule endomicroscope 15 is pressed against the tissue 30.

For example, the recess 27 allows intestinal villi of a small intestine to adopt their physiological configuration during the image acquisition process. With conventional capsule endomicroscopes the intestinal villi are pressed flat into an abnormal position during image acquisition which does not allow for visualizing the intestinal villi in their native configuration. This makes it impossible to detect pathologies in the three-dimensional configuration or shape of the intestinal villi, as present e.g. in celiac disease.

During the use of the capsule endomicroscope the small intestine can be filled with a water-like liquid, for example polyethylene glycol. In this case the spaces 24 between the endomicroscope surface 9 and the tissue surface 23 are filled with a clear liquid characterized by a significantly smaller difference in refractive index relative to the optically transparent material 1, than for example air.

In this case the refractive interface formed at the capsule endomicroscope surface 9 and the polyethylene glycol has less negative impact on the illumination and image acquisition than an interface between the surface 9 and air would have. This is indicated in FIG. 7 by a dashed line of the capsule surface 9 between the optically transparent material 1 and the spaces 24.

Additionally, the capsule endomicroscope 15 can comprise a contact sensing unit configured to detect the presence of tissue 30 in the direct proximity of the contact imaging unit 17/image acquisition area 12.

This serves to prevent image acquisition in a state in which no tissue 30 is present in the image acquisition area 12/capsule surface 9 in a desired proximity or in direct contact with the image acquisition area 12/capsule surface 9. This is especially advantageous in order to avoid energy usage in times where no tissue is close enough to the capsule endomicroscope in order to generate useful data.

Further additionally, the capsule endomicroscope 15 may comprise a context image acquisition assembly/lumen imaging unit 21, that captures the lumen of a hollow organ, especially at that point in time at which also the contact imaging unit 17 captures close-up images of the tissue surface.

This serves the purpose to provide a context to the images captured by the contact imaging unit 17 in order to improve the quality of diagnosis. For example, the absence of intestinal villi is entirely normal in some sections of the intestinal tract whereas in other sections of the intestinal tract such an absence of intestinal villi is strongly indicative of a disorder.

As shown in FIG. 8, the center of gravity 31 of the capsule 15 need not coincide with the geometric center point 32 of the capsule 15. The center of gravity 31 of the capsule 15 is preferentially shifted from the geometric center point 32 of the capsule endomicroscope 15 in the direction towards the contact imaging unit 17.

This leads to a tilted orientation of the capsule 15 in space, in which that side of the capsule endomicroscope 15 on which the contact imaging unit 17 arranged is brought into direct proximity or into direct contact with the tissue surface 23.

This can be achieved by positioning components of high density (for example batteries) on a side of the capsule endomicroscope 15 which also comprises the contact imaging unit 17 or by creating spaces of low density (for example air) at that side of the capsule endomicroscope 15 opposite to the contact imaging unit 17.

The geometric center point 32 of the capsule endomicroscope 15 coincides with the center of gravity 31, when the capsule endomicroscope 15 completely consists of material of equal and constant density.

The invention claimed is:

1. A capsule endomicroscope having a predetermined axial length and a diameter which is smaller than the axial length the capsule endomicroscope being adapted to acquire images of a surface of a hollow organ, the capsule endomicroscope comprising:

a microscopic image acquisition assembly having an optical axis orientated in a radial direction of the capsule endomicroscope in a way to acquire microscopic images of a section of the surface of the hollow organ present in a predetermined image acquisition area on a radial outer surface of the capsule endomicroscope through a housing of the capsule endomicroscope consisting of at least sectionally light-transparent material, and a light source adapted to emit light rays in the radial direction of the capsule endomicroscope through the light-transparent material of the housing during image acquisition, wherein light-transparent material of the housing is located between the light source and the predetermined image acquisition area, and wherein the light source and the light-transparent material of the housing are interconnected to each other such that refraction interfaces between the light source and the predetermined image acquisition area are avoided, wherein the light source is directly incorporated or embedded or molded into a separate component of a light-transparent material and said separate component is directly incorporated or embedded or molded into the light-transparent material of the housing, and wherein the light-transparent material of the separate component and the light-transparent material of the housing have essentially the same refractive index.

2. The capsule endomicroscope according to claim 1, wherein the light source is directly incorporated or embedded or molded into the light-transparent material of the housing.

3. The capsule endomicroscope according to claim 1, wherein the microscopic image acquisition assembly is arranged in a lumen provided within the housing or inside the light-transparent material of the housing wherein a separate distortion prevention component is provided above the microscopic image acquisition assembly when seen in the direction of the optical axis, the separate distortion prevention component is interconnected with the light-transparent material of the housing to form an upper boundary of the lumen when seen in the direction of the optical axis and is adapted to prevent any refraction interface from arising at the boundary between a fluid present in the lumen and the distortion prevention component.

4. The capsule endomicroscope according to claim 3, wherein the distortion prevention component has on its one side forming an upper boundary of the lumen a predetermined surface structure being different than a structure of an inside surface of the housing and being adapted to reduce refraction at a surface of the distortion prevention component.

5. The capsule endomicroscope according to claim 1, wherein a center of gravity of the capsule endomicroscope is displaced from a geometric center point of the capsule endomicroscope.

6. The capsule endomicroscope according to claim 5, wherein the center of gravity of the capsule endomicroscope is displaced from the geometric center point of the capsule endomicroscope towards a position of the image acquisition area on the radial outer surface of the capsule endomicroscope.

7. The capsule endomicroscope according to claim 1, further comprising a recess at the radial outer surface of the capsule endomicroscope, a position of said recess at least in part coinciding with a position of the image acquisition area on the radial outer surface of the capsule endomicroscope.

8. The capsule endomicroscope according to claim 1, further comprising a proximity detection assembly configured to detect the presence of an object in the immediate proximity of the image acquisition area and, if said detection result is positive, activate the microscopic image acquisition assembly and the light source accordingly.

9. The capsule endomicroscope according to claim 1, further comprising a macroscopic context image acquisition assembly adapted to acquire macroscopic images of larger surroundings of the capsule endomicroscope, simultaneously with an image acquisition operation of the microscopic image acquisition assembly.

10. The capsule endomicroscope according to claim 1, wherein the light source is interconnected with the light-transparent material of the housing by casting or moulding or grouting or potting or press-fitting or embedding or directly via an intermediate coupling fluid having essentially the same refractive index as the light-transparent material of the housing.

11. The capsule endomicroscope according to claim 1, wherein the light-transparent material of the housing constitutes an outer layer of the housing of the capsule endomicroscope.

* * * * *